United States Patent
Kane et al.

(10) Patent No.: US 9,201,112 B2
(45) Date of Patent: Dec. 1, 2015

(54) ATOM PROBE TOMOGRAPHY SAMPLE PREPARATION FOR THREE-DIMENSIONAL (3D) SEMICONDUCTOR DEVICES

(71) Applicant: International Business Machines Corporation, Armonk, NY (US)

(72) Inventors: Terence L. Kane, Wappingers Falls, NY (US); John M. Walsh, New Windsor, NY (US)

(73) Assignee: International Business Machines Corporation, Armonk, NY (US)

( * ) Notice: Subject to any disclaimer, the term of this patent is extended or adjusted under 35 U.S.C. 154(b) by 163 days.

(21) Appl. No.: 14/100,343

(22) Filed: Dec. 9, 2013

(65) Prior Publication Data

US 2015/0160286 A1 Jun. 11, 2015

(51) Int. Cl.
*G01R 31/26* (2014.01)
*G01Q 30/20* (2010.01)
*H01J 37/317* (2006.01)
*G01Q 60/40* (2010.01)

(52) U.S. Cl.
CPC ........ *G01R 31/2644* (2013.01); *G01R 31/2621* (2013.01); *H01J 37/317* (2013.01); *G01Q 60/40* (2013.01); *H01J 2237/31749* (2013.01)

(58) Field of Classification Search
CPC .............. G01R 31/26; G01R 31/2601; G01R 31/2621; G01R 31/2644; G01Q 30/00; G01Q 30/02; G01Q 30/20; G01Q 60/24; G01Q 60/36; G01Q 60/363; H01L 22/00; H01L 22/10; H01L 22/12; H01L 22/14; H01L 22/20
USPC ...................... 250/306–443.1; 438/10, 14, 17
See application file for complete search history.

(56) References Cited

U.S. PATENT DOCUMENTS

| 6,789,032 | B2 | 9/2004 | Barbour et al. | |
|---|---|---|---|---|
| 7,139,944 | B2 | 11/2006 | Barbour et al. | |
| 7,194,366 | B2 | 3/2007 | Singh et al. | |
| 7,323,890 | B2 | 1/2008 | Petersen et al. | |
| 7,409,306 | B2 | 8/2008 | Singh et al. | |
| 7,451,646 | B2 | 11/2008 | Cleland et al. | |
| 7,893,703 | B2 | 2/2011 | Rzepiela et al. | |
| 2006/0084211 | A1* | 4/2006 | Yang et al. | 438/197 |
| 2006/0152232 | A1 | 7/2006 | Shvets et al. | |
| 2008/0185650 | A1* | 8/2008 | Chen et al. | 257/348 |
| 2010/0163727 | A1 | 7/2010 | Bell et al. | |
| 2012/0146669 | A1 | 6/2012 | Erickson | |
| 2012/0292715 | A1* | 11/2012 | Hong et al. | 257/392 |
| 2013/0214468 | A1* | 8/2013 | Giannuzzi | 269/287 |
| 2014/0353497 | A1* | 12/2014 | Demarest et al. | 250/307 |
| 2015/0137003 | A1* | 5/2015 | Liew | 250/453.11 |

\* cited by examiner

*Primary Examiner* — Jack Berman
*Assistant Examiner* — David E Smith
(74) *Attorney, Agent, or Firm* — Keivan Razavi; Steven Meyers

(57) ABSTRACT

A method for atom probe tomography (APT) sample preparation from a three-dimensional (3D) field effect transistor device formed within a semiconductor structure is provided. The method may include measuring a capacitance-voltage (C-V) characteristic for the 3D field effect transistor device and identifying, based on the measured capacitance-voltage (C-V) characteristic, a Fin structure corresponding to the 3D field effect transistor device. The identified Fin structure is detached from the 3D field effect transistor device using a nanomanipulator probe tip. The detached Fin is then welded to the nanomanipulator probe tip using an incident focused ion beam having a voltage of less than about 1000 eV. The incident focused ion beam having a voltage of less than about 1000 eV is applied to a tip of the Fin that is welded to the nanomanipulator probe tip. The tip of the Fin may then be sharpened by the focused ion beam.

20 Claims, 11 Drawing Sheets

US 9,201,112 B2

ATOM PROBE TOMOGRAPHY SAMPLE PREPARATION FOR THREE-DIMENSIONAL (3D) SEMICONDUCTOR DEVICES

BACKGROUND a. Field of the Invention

The present invention generally relates to semiconductor device testing, and more particularly, to the preparation of a device under test (DUT) during such semiconductor device testing.

b. Background of Invention

Semiconductor device performance may be measured using a myriad of techniques and instruments. For example, in order to perform Atomic Force Probing (AFP) of a semiconductor device or structure, various layers may need to be removed for exposing the device or structure's contacts (e.g., tungsten studs) or surface prior to probing. Such layer removal or delayering may be carried out using either more coarse methods such as chemical mechanical polishing (CMP) or relatively high-precision techniques employing, for example, focused or collimated high-energy (>500 eV) ion beam etching. Such delayering techniques may, however, damage the device or structure's surface, or alternatively, introduce unwanted irregularities (e.g., unwanted ion implantation) into the device or structure. For example, the process used to prepare the device or structure prior to test or evaluation may undesirably introduce defects (e.g., gallium ion implantations due to high energy ion beam etching) or produce shifts in performance characteristics (e.g., MOSFET threshold voltage ($V_t$) shifts). This may subsequently be misconstrued as a device characteristic resulting from fabrication processes as opposed to a measurement induced defect.

BRIEF SUMMARY

It may, therefore, be desirable, among other things, to prepare a sample (e.g., a Fin) of a three-dimensional (3D) DUT (e.g., FinFet device) for characteristic testing by preserving the electrical integrity of such a DUT during the sample preparation process.

According to at least one exemplary embodiment, a method for atom probe tomography (APT) sample preparation from a three-dimensional (3D) field effect transistor device formed within a semiconductor structure is provided. The method may include measuring a capacitance-voltage (C-V) characteristic for the 3D field effect transistor device; identifying, based on the measured capacitance-voltage (C-V) characteristic, a Fin structure corresponding to the 3D field effect transistor device; detaching the identified Fin structure from the 3D field effect transistor device using a nanomanipulator probe tip; welding the detached Fin to the nanomanipulator probe tip using an incident focused ion beam having a voltage of less than about 1000 eV; and applying the incident focused ion beam having a voltage of less than about 1000 eV to a tip of the Fin that is welded to the nanomanipulator probe tip. The tip of the Fin may be sharpened by the focused ion beam.

According to at least one other exemplary embodiment, a method for atom probe tomography (APT) sample preparation from a three-dimensional (3D) field effect transistor device formed within a semiconductor structure is provided. The method may include applying a voltage in the range of about 50 eV to less than 300 eV to an inductively coupled Argon ion source operating at a radio frequency; generating, from the Argon ion source, a collimated ion beam incident on a crystalline surface of the semiconductor structure for planar removal of layers of the crystalline surface, whereby the collimated ion beam minimizes surface amorphization of the crystalline surface of the semiconductor structure; exposing first and second contact regions underlying the crystalline surface associated with the 3D field effect transistor device using an end-point detector based on the planar removal of the layers; coupling a high-frequency impedance probe having a frequency range of about 5 Mhz to about 110 Mhz to an impedance analyzer; coupling the high-frequency impedance probe to a first and a second atomic force probe tip; coupling, using an atomic force microscope, the first atomic force probe tip to the exposed first contact region; coupling, using the atomic force microscope, the second atomic force probe tip to the exposed second contact region; measuring the C-V characteristic for the 3D field effect transistor device on the impedance analyzer, the impedance analyzer applying an operating frequency corresponding to the frequency range of about 5 Mhz to about 110 Mhz to the first and second contact regions associated with the 3D field effect transistor device using the high-frequency impedance probe; and detaching, based on the measured C-V characteristic, a Fin structure from the 3D field effect transistor device using a nanomanipulator probe tip, the detached Fin being both welded to the nanomanipulator probe tip and shaped using an incident focused ion beam having a voltage of less than about 1000 eV.

According to yet another exemplary embodiment, a method for atom probe tomography (APT) sample preparation from a three-dimensional (3D) field effect transistor device formed within a semiconductor structure is provided. The method may include identifying, based on a capacitance-voltage (C-V) characteristic measurement, a Fin structure corresponding to the 3D field effect transistor device; removing a hardmask layer from a top surface of the Fin structure using a collimated ion beam generated by applying a voltage in the range of about 50 eV to less than 300 eV to an inductively coupled Argon ion source operating at a radio frequency; applying a metallic coating to the Fin structure; detaching the coated Fin structure from the 3D field effect transistor device using a nanomanipulator probe tip; welding the detached coated Fin to the nanomanipulator probe tip using an incident focused ion beam having a voltage of less than about 1000 eV; and applying the incident focused ion beam having a voltage of less than about 1000 eV to a tip of the Fin that is welded to nanomanipulator probe tip, whereby the tip of the Fin is sharpened by the focused ion beam.

BRIEF DESCRIPTION OF THE SEVERAL VIEWS OF THE DRAWINGS

The drawings are not necessarily to scale. The drawings are merely schematic representations, not intended to portray specific parameters of the invention. The drawings are intended to depict only typical embodiments of the invention. In the drawings, like numbering represents like elements.

DETAILED DESCRIPTION

The following one or more exemplary embodiments describe, among other things, a low energy ion beam milling apparatus and method utilized for the purpose of delayering the surfaces of semiconductor devices for subsequent testing and characterization of such devices. The delayering of various surfaces of semiconductor devices, particularly three-dimensional semiconductor devices such as discrete FinFet transistor devices, may inadvertently introduce defects and unwanted artifacts within the devices. For example, a high-energy 500 eV focused gallium ion beam may, during the milling and delayering process of a FET device, cause a shift in the threshold voltage ($V_t$) of the FET device. Additionally, the high-energy ion beam may alter dopant density or dopant distribution. In all such cases, the device may be characterized incorrectly as a result of the induced irregularities or defects that are inadvertently introduced into the semiconductor device under tests based on the ion beam milling process.

Also, the following one or more exemplary embodiments describe, among other things, a capacitance-voltage (C-V) characteristic measurement system and method following the exposing of the contact regions of a discrete device (e.g., FinFet device) using the low energy ion beam milling apparatus. More particularly, as emerging semiconductor technology nodes continue to drive semiconductor device (FinFet(s), planar Fet(s), etc.) dimensionality down, these reduced geometry devices may present measurement challenges during AC characteristic measurements. Thus, an enhanced technique for measuring AC characteristics such as the capacitance-voltage (C-V) characteristic is described by the following exemplary embodiments.

Moreover, the following one or more exemplary embodiments describe, among other things, a second ion milling process, whereby following a delayering of the surfaces of a 3D semiconductor device (e.g., a FinFet device), a low energy focused ion beam (FIB) may be utilized to create a prepared sample (e.g., a Fin of the FinFet device) for analysis by, for example, an Atom Probe Tomography (ATP) tool. More specifically, for example, a C-V characteristic measurement may provide a determination as to whether to prepare the sample for further analysis and testing using the second FIB ion milling process.

Figure 1:
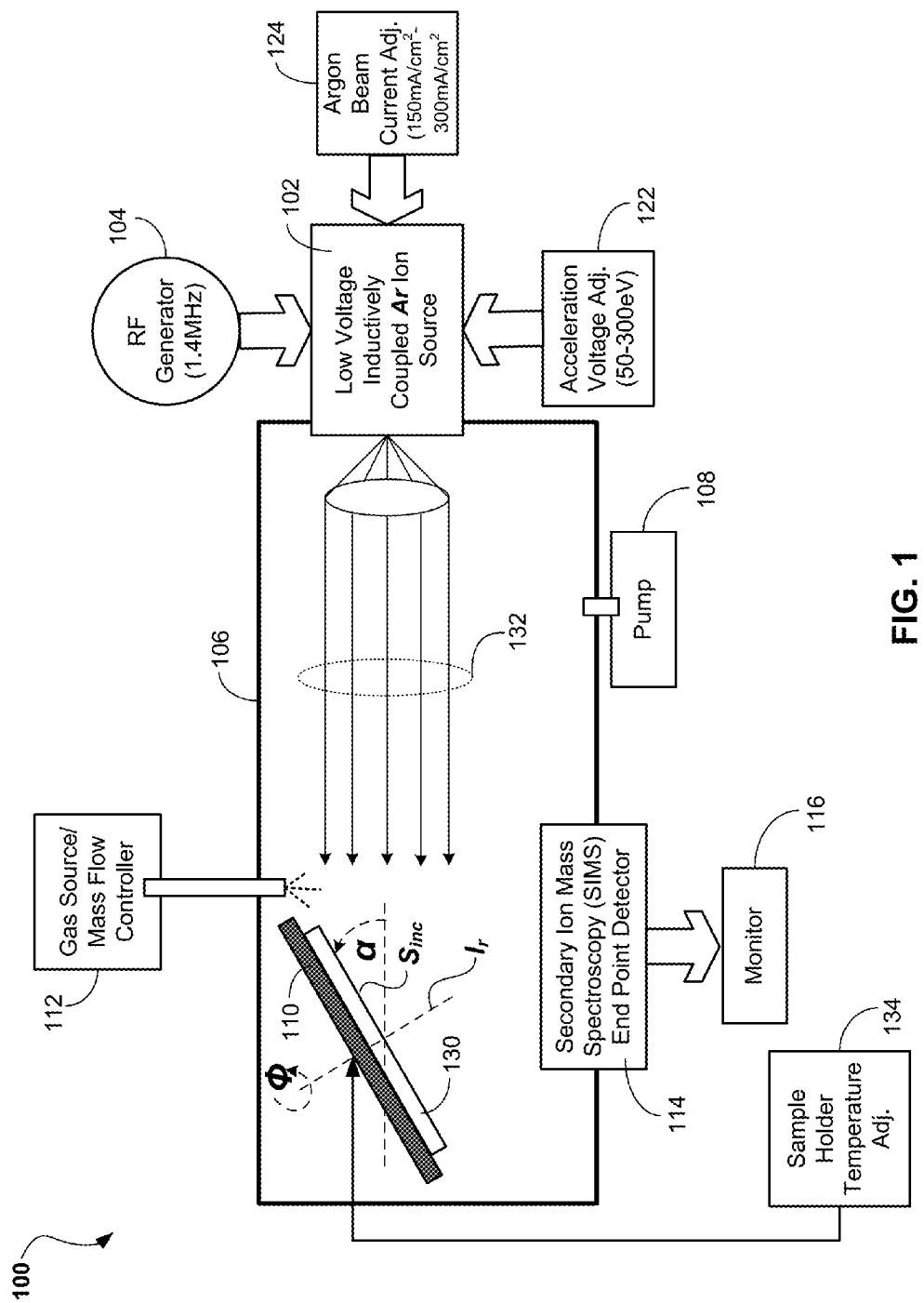
FIG. 1 is a system diagram of an ion beam milling apparatus according to an exemplary embodiment.

Referring to FIG. 1, a system diagram of an ion beam milling apparatus 100 according to an exemplary embodiment is depicted. The ion beam milling apparatus 100 may include a low voltage inductively coupled Argon (Ar) ion source 102, an RF signal source 104, a chamber 106 (e.g., stainless steel), a pump 108, a semiconductor device holder 110, a gas source/mass flow controller 112, a secondary ion mass spectroscopy (SIMS) end point detector 114, and an optional monitor 116 coupled to the SIMS detector 114.

As illustrated, a radio frequency (RF) signal source 104 generates a 1.4 MHz RF signal that is applied to the low voltage inductively coupled Argon (Ar) ion source 102. The low voltage inductively coupled Argon (Ar) ion source 102 also includes a means for adjusting the acceleration voltage 122 of the low voltage inductively coupled Argon (Ar) ion source 102 and a means for adjusting the Ar beam current 124 of the low voltage inductively coupled Argon (Ar) ion source 102.

The semiconductor device holder 110 may hold a semiconductor device under test (DUT) 130. The device holder 110 may accordingly have an adjustable angular orientation ($\alpha$) relative to an incident collimated ion beam 132 generated by the low voltage inductively coupled Argon (Ar) ion source 102. In addition to the angular orientation ($\alpha$), the semiconductor device holder 110 also rotates about its own axis, as denoted by $I_r$, at an adjustable rotational speed ($\phi$). The semiconductor device holder 110 may also include a means for adjusting its temperature 134.

In operation, the low voltage inductively coupled Argon (Ar) ion source 102 generates an inert low-energy collimated Ar ion beam 132 that is incident upon the DUT 130 that is placed and secured in the device holder 110. As shown in FIG. 1, the inert low-energy collimated ion beam 132 is incident upon DUT 130 at angular orientation $\alpha$. As the inert low-energy collimated ion beam 132 mills and, therefore, delayers incident surface $S_{inc}$ of the DUT 130, secondary ions generated at the surface $S_{inc}$ being etched are detected by the SIMS detector 114. The generated secondary ions may, for example, have characteristics such as mass-to-charge ratio which may differ based on the different layers of material that may be encountered during the milling operation. This distinction in characteristics may be used in order to provide a precise determination of the layer being milled. Using, for example, pulse counting, the SIMS detector 114 may generate a SIMS trace of counts per second (i.e., c/s) over time (i.e., t) for the detected secondary ions generated during the ion milling. These traces may be displayed graphically on monitor 116. Other diagnostic tools such as Fast Fourier Transform (FFT) analysis may be included with the SIMS detection process.

Based on the DUT 130 and the material that is to be delayered by the ion beam milling apparatus 100, different operating regimes may be employed by, for example, adjusting the acceleration voltage via adjustment means 122, adjusting the Ar beam current via adjustment means 124, adjusting the device holder 110 temperature via adjustment means 134, adjusting the chamber 106 pressure via pump 108, setting the angular orientation ($\alpha$) and rotational speed ($\phi$) of the device holder 110, applying an RF signal to the low voltage inductively coupled Argon (Ar) ion source 102, and the application (optionally) of etch selective gases via the gas source/mass flow controller 112. For example, etch selective hexafluoroethane ($C_2F_6$) gas may be used for removing silicon nitride hardmask materials and etch selective tetrafluoromethane ($CF_4$) gas may be used for removing silicon oxide ($SiO_2$). In the context of ion beam milling and Atomic Force Probing (AFP), both silicon oxide and silicon nitride layers may cause damage to the probes used in the AFP process. Thus, these layers are removed prior to AFP. As described in the following, the DUT 130 may include a 3D semiconductor structure such as a FinFet device.

Figure 2:
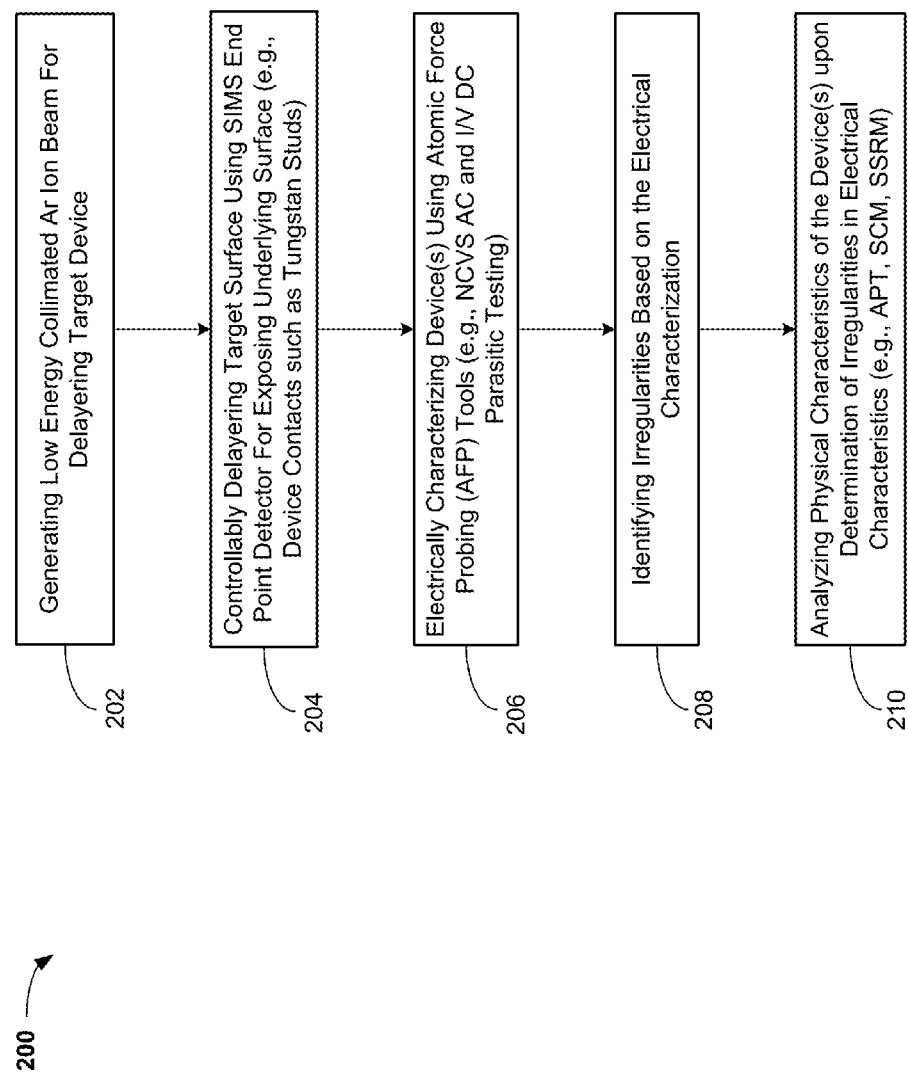
FIG. 2 is a process flow diagram corresponding to a testing process associated with a semiconductor structure according to an exemplary embodiment.

FIG. 2 is a process flow diagram 200 corresponding to a testing process associated with a semiconductor structure according to an exemplary embodiment. At 202, a low-energy collimated inert Ar ion beam may be generated by an apparatus, such as apparatus 100 (FIG. 1), for delayering a target device under test (DUT).

At 204, based on the generated low-energy collimated inert Ar ion beam (202), a controlled delayering of the target surface of the DUT is accomplished using, for example, a SIMS endpoint detector such as SIMS detector 114 (FIG. 1). For example, layers of copper my be removed by the generated low-energy collimated inert Ar ion beam in order to expose the tungsten studs corresponding to a Field Effect Transistor (FET) selected for characterization testing. Once exposed, using AFP, the tungsten studs may be probed for characterizing the FET device. Alternative examples may include delayering silicon nitride or silicon oxide layers that have been deposited on three-dimensional (3D) semiconductor structures such the Fins of FinFET type devices. In this example, the 3D structure may be especially susceptible to the impact of a high-energy ion beam milling process. For example, the electrical probing (e.g., Atomic Force Probing) of a Fin structure may require the removal of a silicon nitride hard mask (i.e., with etch selective hexafluoroethane gas—$C_2F_6$) located on the top surface of the Fin. Since the Fin may have a thickness dimension in the region 10-15 nm, an incident high-energy ion beam (e.g., >500 eV) may cause amorphization damage to the Fin, which in turn may be reflected in the subsequently obtained characterization results (e.g., current-voltage I/V curves, APT measurements, SSRM measurements, SCM measurements, etc.) associated with the device (i.e., FinFET device).

At 206, once the desired area or surface of the DUT is exposed (204), the device may be electrically characterized using Atomic Force Probing (AFP) tools such as, but not limited to, Nanoprobe Capacitance-Voltage (C-V) Spectroscopy (NCVS) AC based parasitic testing and Current-Voltage (I/V) DC based parasitic testing.

As further described below, an enhanced C-V nanoprobe apparatus (e.g., see FIGS. 4-5) may be utilized in order to provide C-V measurements at the level of discrete devices. For example, a discrete 3D device such as a FinFET may be ion milled using the above described ion beam milling apparatus 100 (FIG. 1) in order to expose contact regions associated with the device.

At 208, any irregularities or characteristic defects in the DUT may be identified based on an evaluation of the results of the electrical characterization obtained during the AFP process (206). Based on the detection of such irregularities or defects (208), at 210, the physical characteristic of the DUT are further evaluated using, for example, Atomic Probe Tomography (APT), Scanning Capacitance Microscopy (SCM), and/or Scanning Spreading Resistance Microscopy (SSRM). AFT may be utilized to determined doping concentration, while SSRM techniques may be indicative of dopant distribution associated with the DUT. SCM may be used to evaluate carrier density.

Figure 3:
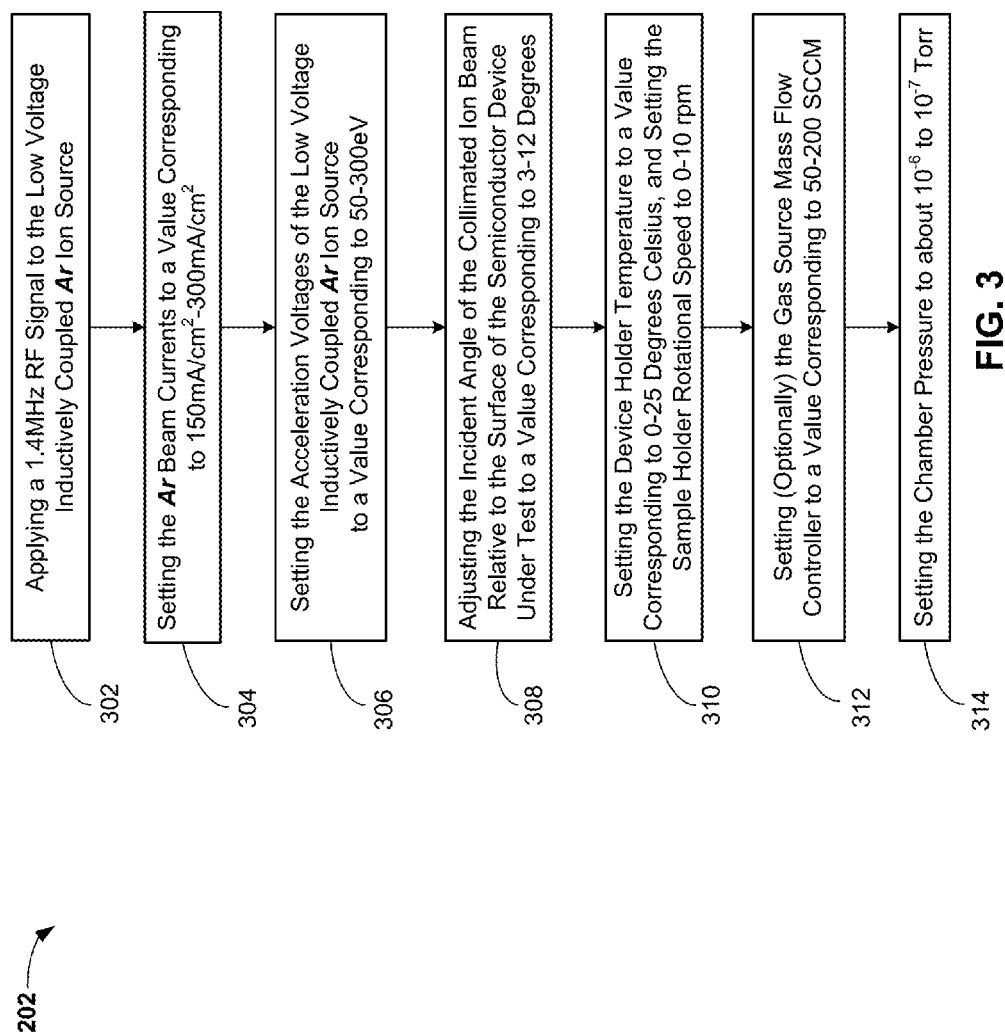
FIG. 3 is flow diagram corresponding to configuring the ion beam milling apparatus of FIG. 1 according to an exemplary embodiment.

FIG. 3 is flow diagram 202 corresponding to configuring the ion beam milling apparatus of FIG. 1 according to an exemplary embodiment. The following settings allow the generation of a collimated low-energy (<300 eV) inert Ar ion beam that provides delayering without altering the characteristics of the device under test (DUT). The settings include a range of values based on the DUT and the material that is being delayered. The flow diagram 202 of FIG. 3 is described with the aid of FIG. 1.

At 302, a radio frequency signal of 1.4 MHz or approximately 1.4 Mhz is applied to the low voltage inductively coupled Argon (Ar) ion source 102. The Ar Beam current may be set to a value between 150 mA/cm$^2$–300 mA/cm$^2$ (304). The acceleration voltage of the low voltage inductively coupled Argon (Ar) ion source 102 may be set to a value of about 50 eV to a value less than 300 eV (306).

At 308, the incident angle α between the incident collimated Ar beam 132 and the surface $S_{inc}$ of the DUT 130 that is held by semiconductor device holder 110 within the stainless steel chamber 106 may be adjusted to be around 3-12 degrees. Greater or lesser angles may also be contemplated.

At 310, the device holder 110 temperature may be adjusted to be about 0-25 degrees Celsius, while the device holder 110 rotational speed (ϕ) may be varied to be between about 0-10 revolutions per minute (rpm). At 312, depending on the material that is being delayered, etching gas (e.g., $C_2F_6$, $CF_4$) may be applied within the chamber 106 at a flow rate of between 50 to about 200 standard cubic centimeters per minute (SCCM). For example, in some instances etching gases may not be utilized. One example of not using an etch-selective gas may be during the delayering of copper material for exposing tungsten studs prior to the AFP process. At step 314, the chamber pressure may be set to be about $10^{-6}$ to about $10^{-7}$ Torr, although lesser or greater pressures may also be contemplated.

It may be appreciated that the various processes of FIG. 3 may be carried out in no particular order prior to delayering the DUT 130. As previously mentioned, the various adjustment parameters described in relation to FIG. 3 may be set and, in some instances, readjusted based on DUT type (e.g., 3D devices such as FinFETs) and/or the material on the DUT being delayered (e.g., copper, silicon nitride, etc.).

Once exposed using the milling apparatus 100, an enhanced C-V nanoprobe apparatus may determine the C-V characteristic and, therefore, various electrical anomalies. As the geometry of the discrete devices reduce, their corresponding sensitivity for obtaining C-V characteristics accordingly reduces. The following described embodiments may, therefore, enhance, among other things, measurement sensitivity for obtaining the C-V characteristics of such discrete semiconductor devices as their geometries shrink with technological advancements.

Figure 4A:
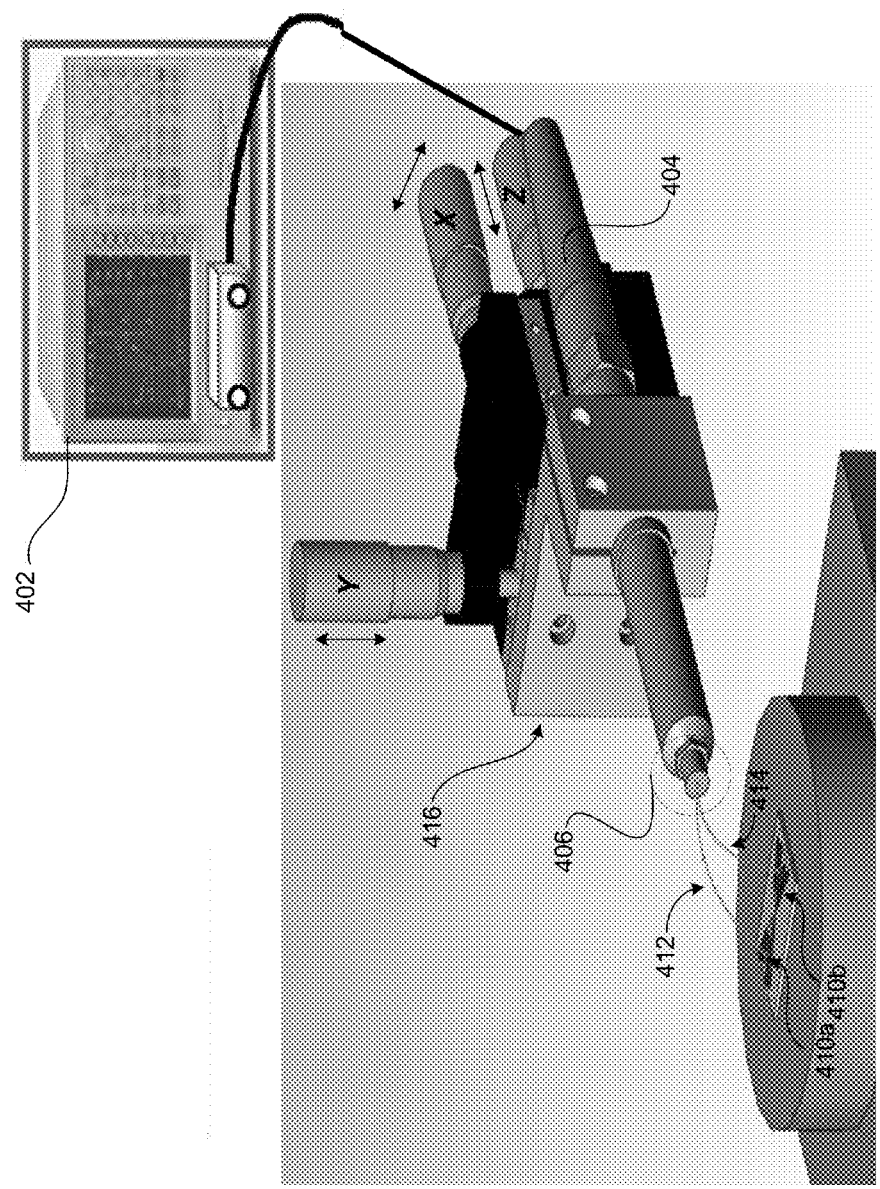
FIG. 4A is a perspective view of atomic force probe tips of an atomic force prober apparatus during C-V characteristic measurements according to an exemplary embodiment.
Figure 4B:
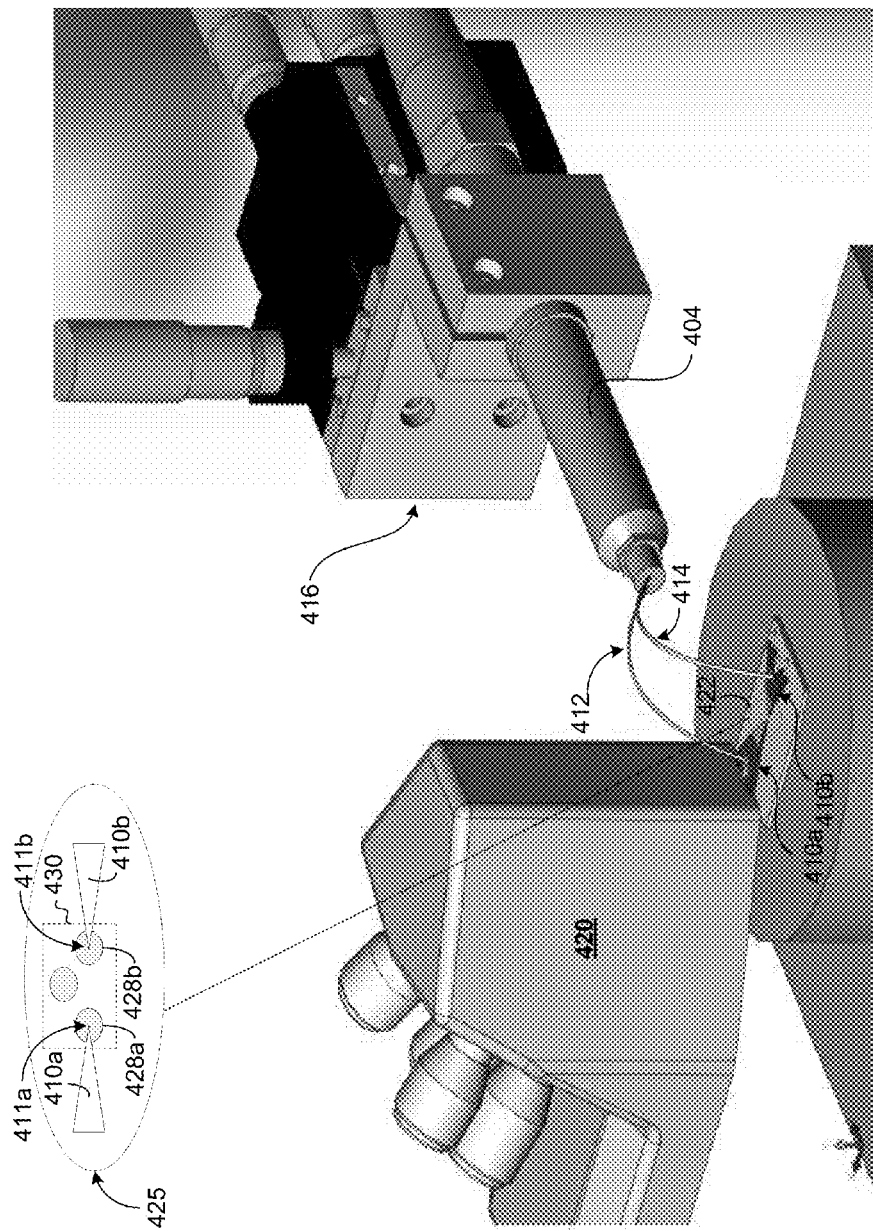
FIG. 4B is yet another perspective view of atomic force probe tips of an atomic force prober apparatus during C-V characteristic measurements according to an exemplary embodiment.

FIGS. 4A-4B is a perspective view of atomic force probe tips of an atomic force prober apparatus during C-V characteristic measurements according to an exemplary embodiment. Referring to FIG. 4A, an impedance analyzer 402 such as, for example, a 4294A precision impedance analyzer manufactured by Agilent Technologies®, headquartered in Santa Clara, Calif., may be coupled to and used to drive a high-frequency impedance probe 404 such as, for example, a 42941A impedance probe also manufactured by Agilent Technologies®. As depicted, the end portion 406 of the high-frequency impedance probe 404 is coupled to a pair of atomic force probe tips 410*a*, 410*b* via, for example, a SMA type cable arrangement.

The SMA type cable arrangement may include SMA cable 412 and SMA cable 414, whereby SMA cable 412 may couple to the ground connection of the high-frequency impedance probe 404 and SMA cable 414 may accordingly couple to the signal conductor connection of the high-frequency impedance probe 404. The length of the SMA cables may be selected to be about 5 millimeters (mm) or less in order to, among other things, reduce capacitance losses due to transmission line reflections. In order to configure the impedance analyzer 402 to measure the C-V characteristics at a high-frequency range of about 5 Mhz-110 Mhz, measurement losses should be minimized. Thus, in addition to utilizing a low-loss/short cabling arrangement (e.g., 5 mm SMA cables 412, 414) capable of operating over a frequency range of approximately 5 Mhz-110 Mhz, the tension of the cables 412, 414 may also be manipulated by holding the high-frequency impedance probe 404 with a XYZ manipulation stage 416. More specifically, the tension of the cables 412, 414 may be varied by manipulating the probe 404 along one or more of the X, Y, or Z axes, as depicted. Optimization of the C-V measurement based on tension adjustment may be verified by, for example, viewing the C-V curves captured by the impedance analyzer 402.

Referring to FIG. 4B, a positional manipulation stage 420 associated with an atomic force microscope (not shown) may be used for positioning atomic force probe tip 410a. Likewise, another positional manipulation stage (not shown for illustrative brevity) associated with the atomic force microscope may be used for positioning the other atomic force probe tip 410b. Using the atomic force microscope, the positional manipulation stages (e.g., positioning manipulation stage: 420) may be utilized for coupling the atomic force probe tips 410a, 410b to, for example, exposed contact regions of a discrete device (e.g., FinFET, planar FET, etc.), as indicate at 422. An expanded view 425 of area 422 illustrates atomic force probe tip 410a coupled to an exposed contact region 428a of a discrete device 430 associated with the DUT (e.g., FIG. 1: 130). Similarly, expanded view 425 of area 422 also shows atomic force probe tip 410b coupled to an exposed contact region 428b of the discrete device 430 associated with the DUT (e.g., FIG. 1: 130). For example, exposed contact region 428a may include a source contact region of a FinFet device, while exposed contact region 428b may include a drain contact region of the FinFet device. As described above in relation to the ion milling process, the exposed contact regions 428a, 428b that are probed using the respective atomic force probe tips 410, 410b may be exposed using low energy ion beam milling apparatus 100 (FIG. 1).

As depicted, the electrical cables 412, 414 providing an electrical connection between the impedance probe 404 and the atomic force probe tips 410a, 410b may be made to, for example, a ground and a signal connection at the base portion of the atomic force probe (AFP) tips 410a, 410b. This connection at the base portion is made without impeding the movement of the cantilever composed of the AFP mirrors (not shown) and the AFP tip ends 411a, 411b (e.g., including tungsten tip ends).

Figure 5:
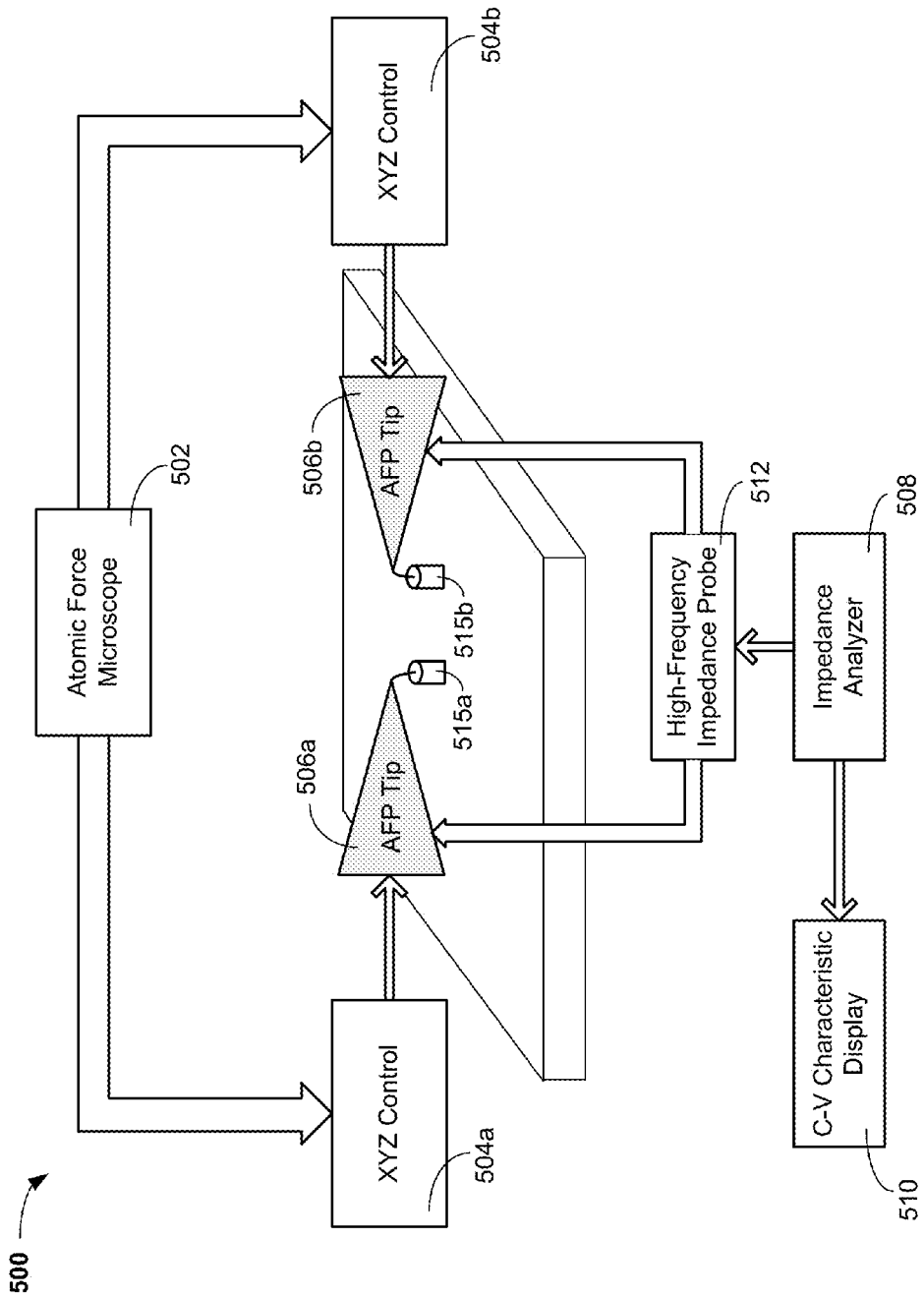
FIG. 5 is a block diagram of a capacitance-voltage (C-V) characteristic measurement system according to an exemplary embodiment.

FIG. 5 is a block diagram of a capacitance-voltage (C-V) characteristic measurement system 500 according to an exemplary embodiment. The capacitance-voltage (C-V) characteristic measurement system 500 may include an atomic force microscope (AFM) 502, positional manipulation stage 504a, atomic force probe (AFP) tip 506a coupled to positional manipulation stage 504a, positional manipulation stage 504b, atomic force probe (AFP) tip 506b coupled to positional manipulation stage 504b, an impedance analyzer 508 configured to generate a C-V characteristic display 510, and a high-frequency impedance probe 512 coupled to the impedance analyzer 508, whereby the high-frequency impedance probe 512 is electrically connected to AFP tips 506a and 506b. It may be appreciated that a more detailed perspective view of the high-frequency impedance probe 512 being electrically coupled to exposed regions 515a and 515b of a discrete device under test (DUT) via AFP tips 506a and 506b is also depicted and described in relation to FIGS. 4A and 4B.

The operation of capacitance-voltage (C-V) characteristic measurement system 500 is described below with the aid of the flow diagram 600 of FIG. 6.

Figure 6:
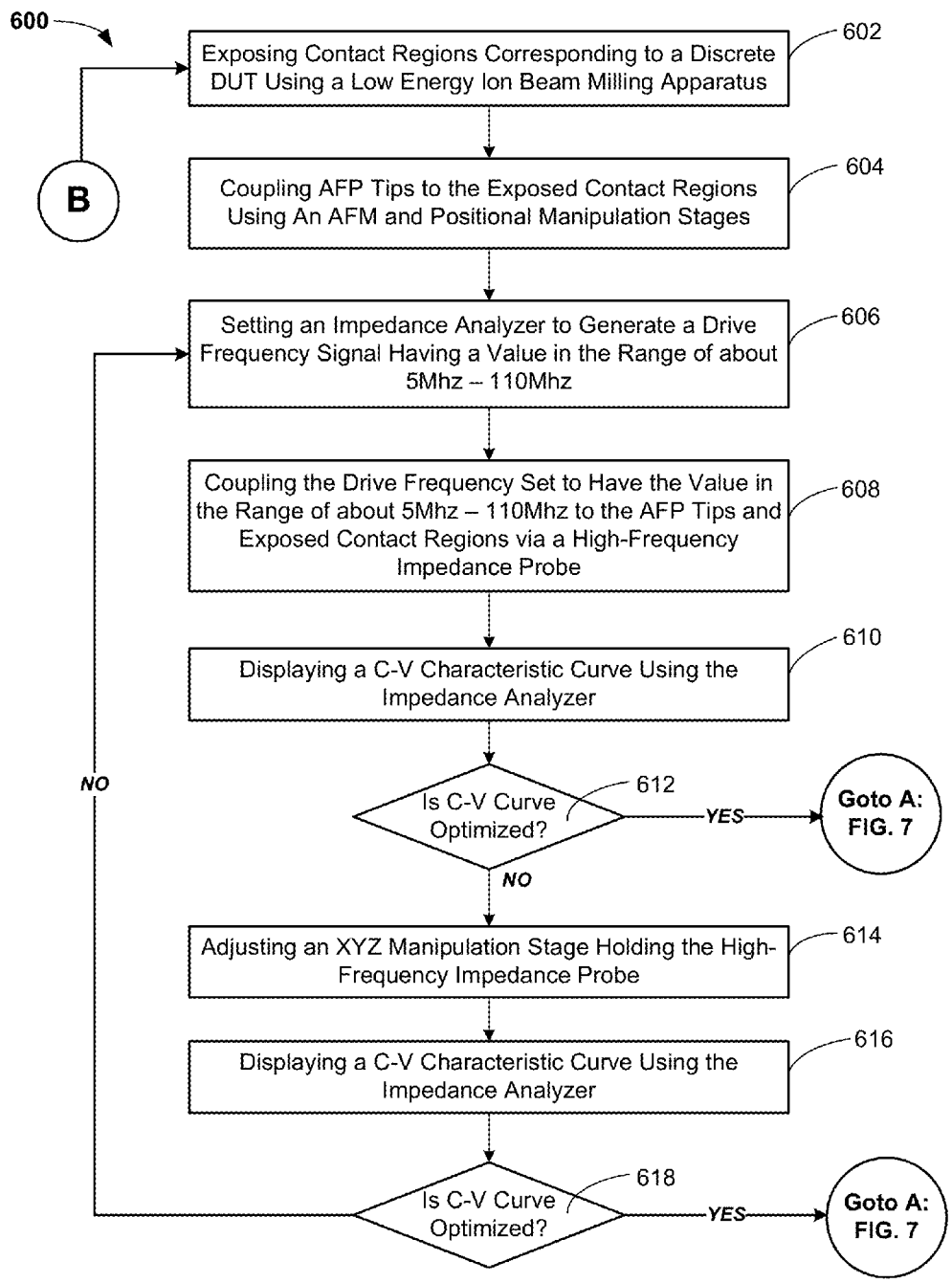
FIG. 6 is an operational flow diagram corresponding to the capacitance-voltage (C-V) characteristic measurement system embodiment depicted in FIG. 5.

Referring to FIG. 6, at 602 the contact regions 515a and 515b of a discrete device under test (DUT) are exposed using a low energy ion beam milling apparatus such as the exemplary embodiment depicted in FIG. 1. As previously described, low energy ion beam milling apparatus 100 (FIG. 1) may provide ion beam milling, while mitigating undesirably introduced defects or produced shifts in performance characteristics (e.g., MOSFET threshold voltage ($V_t$) shifts).

At 604, the AFP tips 506a, 506b are coupled to exposed contact regions 515a and 515b, whereby using the AFM 502, the positional manipulation stages 504a, 504b facilitate electrically connecting the AFP tips 506a, 506b to the exposed contact regions 515a and 515b. Once the electrical connectivity between the exposed contact regions 515a, 515b and the AFP tips 506a, 506b is established, at 606 the impedance analyzer 508 is set to generate a drive frequency signal having a value of about 5 Mhz-110 Mhz. This frequency range may facilitate the provision a high-frequency signal that enables an increased sensitivity when generating C-V measurements on the impedance analyzer 508. This increased sensitivity may be of significance as the physical geometry (e.g., Fin length) of discrete devices (e.g., FinFET) is reduced with advancing node technologies (e.g., 14 nm and below).

At 608, the set drive frequency signal having a value in the range of about 5 Mhz-110 Mhz is coupled from the impedance analyzer 508 to the AFP tips 506a, 506b via high-frequency impedance probe 512. At 610, the C-V characteristic curve of the DUT is generated and displayed using the impedance analyzer 508. If, at 612 it is determined that an optimized C-V curve is generated, the process ends at 620.

Figure 7:
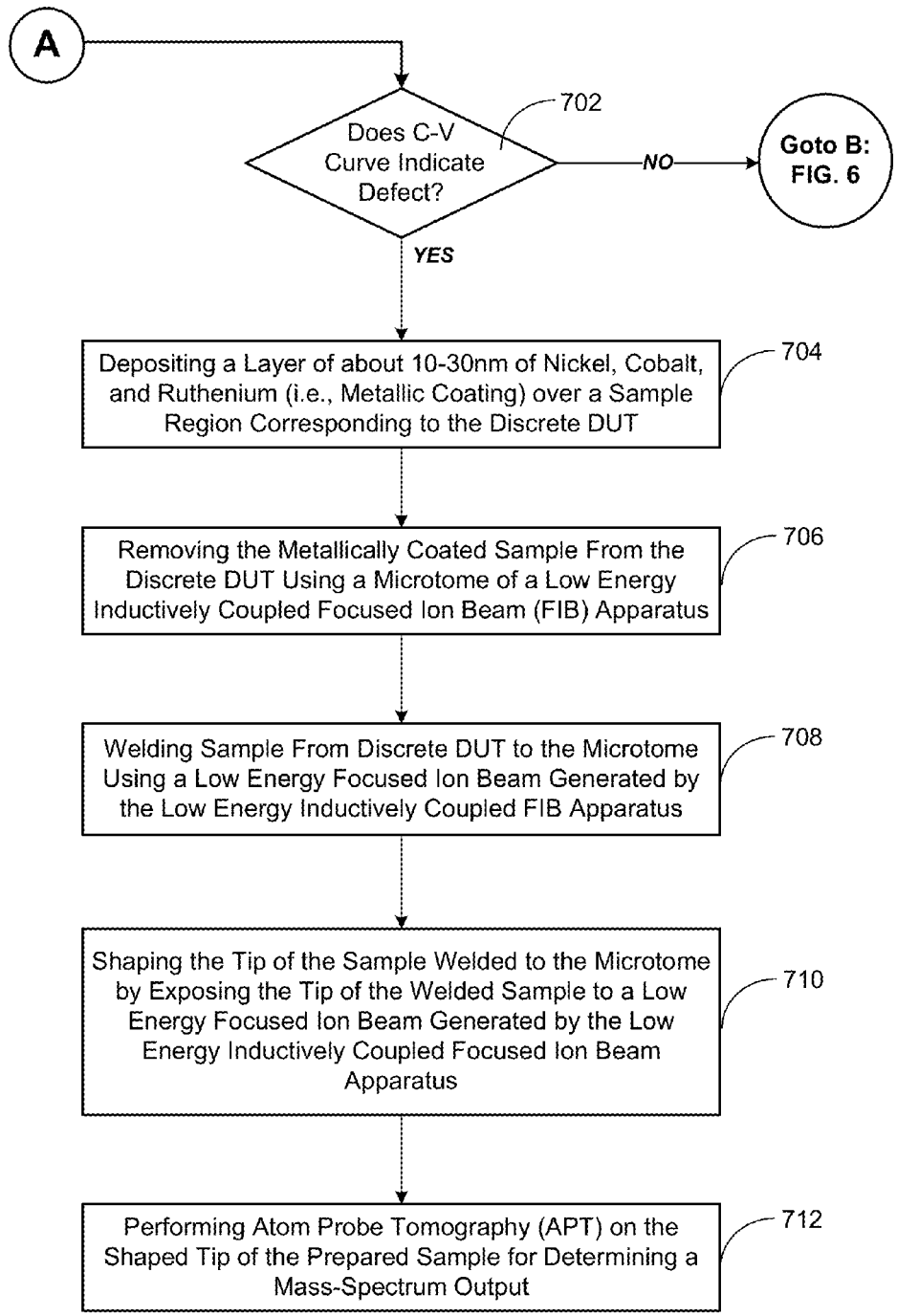
FIG. 7 is an operational flow diagram corresponding to preparing a sample of a DUT for Atom Probe Tomography (APT) according to an exemplary embodiment.

If, however, at 612 it is determined that the C-V curve is not optimized (e.g., no generated C-V curve, etc.), at 614, an XYZ manipulation stage holding the high-frequency impedance probe 512 may be adjusted. Upon adjustment of the XYZ manipulation stage holding the high-frequency probe 512 (614), the C-V characteristic curve of the DUT is again generated and displayed using the impedance analyzer 508 in order to further determine whether an optimized C-V curve is generated (618). If, at 618 an optimized C-V curve is generated, the process goes to 702 (FIG. 7), whereby the C-V curve may be analyzed in order to indicate whether the DUT has a defect. If, however, at 612 it is determined that the C-V curve is optimized (e.g., a satisfactory C-V curve is generated, etc.), the sample preparation process of FIG. 7 is carried out.

An embodiment of a XYZ manipulation stage 416 holding a high-frequency impedance probe 404 is depicted in FIGS. 4A and 4B. Thus, the high-frequency impedance probe 512 represented in the block diagram of FIG. 5 may be implemented in the same, or substantially the same, manner as that depicted and described in relation to FIGS. 4A and 4B. More specifically, as previously described, the tension of the cables 412, 414 coupling the probe 404 to the AFP tips 410a, 410b may be varied by manipulating the probe 404 along one or more of the X, Y, or Z axes, as depicted. Optimization of the C-V measurement based on tension adjustment may, therefore, be verified by, for example, viewing the C-V curves captured by the impedance analyzer 402.

If, at 618 an optimized C-V curve is still not generated, the process returns to 606, whereby the impedance analyzer 508 is set to generate another drive frequency signal having a value of about 5 Mhz-110 Mhz. As described above, the C-V curve optimization process then continues based on processes 610-620. If, however, at 618 it is determined that the C-V curve is optimized (e.g., a satisfactory C-V curve is generated, etc.), the sample preparation process of FIG. 7 is carried out.

Figure 8A:
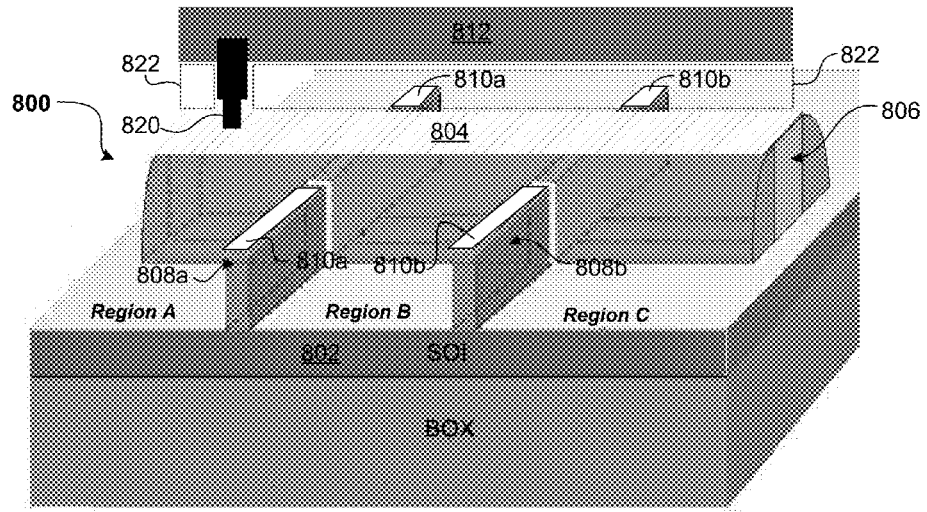
FIGS. 8A and 8B illustrate an exemplary 3D FinFet DUT device used in the sample preparation process of FIGS. 6 and 7 according to an exemplary embodiment.

For example, referring to FIG. 8A, a FinFet DUT 800 3D structure formed on a silicon-on-insulator (SOI) substrate 802 is depicted. The FinFet DUT 800 may include a silicon nitride ($Si_3N_4$) hardmask layer 804 formed on the top surface of gate 806. Also, silicon oxide ($SiO_2$) hardmask layers 808a and 808b may be formed on the top surface of respective Fins 810a and 810b. Although not shown, silicon oxide ($SiO_2$) may also be located between the Fins 810a, 810b, as indicated by Regions A-C. For example, an M1 metal layer 812 may be coupled to the gate 806 via an electrically conductive stud 820 (e.g., tungsten stud). Between the M1 metal layer 812 and the gate 806, an interlayer dielectric (ILD) layer 822 of silicon oxide ($SiO_2$) may also exist.

Using the low-energy collimated inert Ar ion beam generated by apparatus 100 (FIG. 1), M1 metal layer 812 may be delayered. No chemical assisted etch gases may be required during this copper removal process. The silicon oxide ($SiO_2$) material used for the ILD layer 822, the hardmask layers 808a, 808b, and the Regions A-C located between Fins 808a and 808b may also be removed using the low-energy collimated inert Ar ion beam generated by apparatus 100 (FIG. 1). During this $SiO_2$ material removal process, however, a tetrafluoromethane ($CF_4$) etch selective gas may be utilized with the low-energy collimated inert Ar ion beam milling process. Also, the silicon nitride ($Si_3N_4$) hardmask layer 804 formed on the top surface of gate 806 may be delayered using the low-energy collimated inert Ar ion beam generated by apparatus 100 (FIG. 1). For example, an etch selective hexafluoroethane ($C_2F_6$) gas may be used during the low-energy collimated inert Ar ion beam milling process for removal of the silicon nitride ($Si_3N_4$) hardmask layer 804. As described above, the low-energy collimated inert Ar ion beam generated by apparatus 100 (FIG. 1) facilitates the removal of layers associated with the FinFet DUT 800 without introducing unwanted artifacts into the device 800.

Figure 8B:
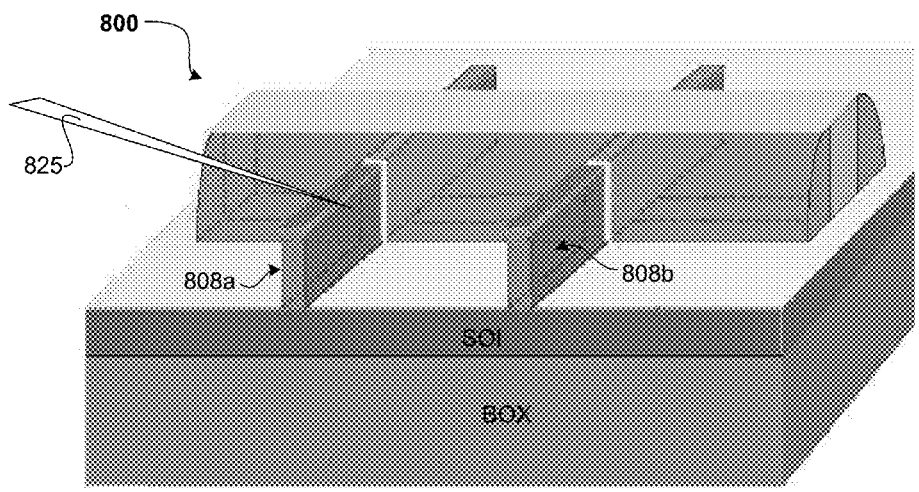

Referring to FIG. 8B, following the ion milling process using apparatus 100 (FIG. 1), processes 602-612 (FIG. 6), and process 702 (FIG. 7), it may be determined (i.e., using C-V curve analysis) whether either of Fins 810a and 810b have electrical characteristic defects that are, for example, correlated with dopant distribution or dopant concentration.

FIG. 7 is an operational flow diagram corresponding to preparing a sample (e.g., FIGS. 8A and 8B: Fins 808a and 808b) of the FinFet DUT 800 (FIGS. 8A and 8B) for Atom Probe Tomography (APT) according to an exemplary embodiment. If at 702, it is determined that the C-V curve indicates no defect in either of Fins 810a and 810b (FIGS. 8A and 8B), the process returns to 602 (FIG. 6), whereby the contacts of other Fins may be exposed using the low energy ion beam milling apparatus of FIG. 1.

However, if at 702 it is determined that the C-V curve indicates a defect in either of Fins 810a and 810b (FIGS. 8A and 8B), at 704, a metallic coating or layer of about 10-30 nm of nickel, cobalt, and ruthenium may then be deposited over, for example, at least the defective Fin (e.g., Fin 810a), which forms a sample. Using the C-V apparatus and method of FIGS. 5 and 6, respectively, C-V curves may be generated by applying the atomic force probe tips 506a, 506b (FIG. 5) to both the source and drain of the FinFet DUT 800 (FIGS. 8A and 8B) via, for example, exposed contact regions 428a and 428b (FIG. 4B).

Figure 9A:
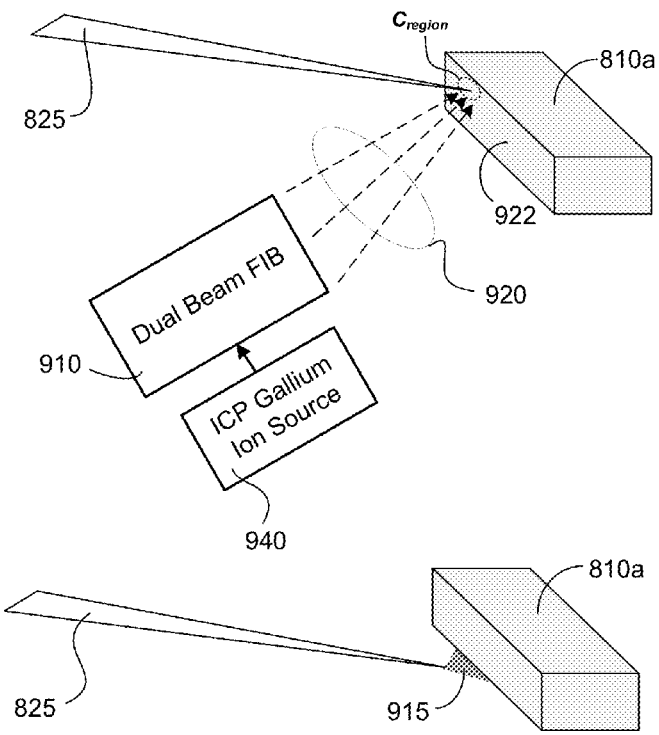
FIGS. 9A-9C illustrate preparing a Fin of a FinFet DUT device as a sample for an APT process.
Figure 9B:
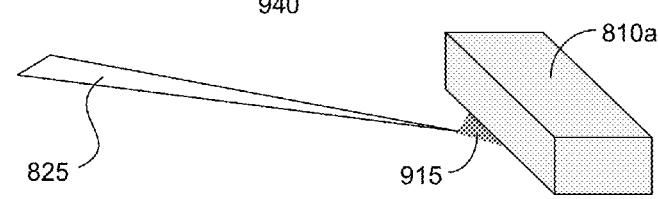

At 706, the metallically coated defective Fin 810a (FIG. 8A) may be removed from the FinFet DUT 800 (FIG. 8A) using a manipulation probe or nanomanipulator 825 (FIG. 8B) such as an OmniProbe®. Referring to FIG. 9A, the nanomanipulator 825 may be used to exert pressure and break the defective Fin 810a away from the FinFet DUT 800 (FIG. 8A). The nanomanipulator 825 may be a tool that forms part of, for example, a known dual beam focused ion beam (DBFIB) apparatus 910. At 708, the defective Fin 810a that is removed from the FinFet DUT 800 (FIG. 8A) is welded, as indicated by 915, to the nanomanipulator 825 using a focused Gallium ion beam 920 generate by the dual beam focused ion beam (DBFIB) apparatus 910. The acceleration voltage of an inductively coupled Gallium (Ga) ion source 940 generating the focused Gallium ion beam 920 may be set to a value in the range of about 500 eV to about 1000 eV. As a result of the metallic coating 922 being located on the outer surfaces of the defective Fin 810a, the application of the focused Gallium ion beam 920 to a contact region $C_{region}$ between the Fin 810a and the tip of the nanomanipulator 825 causes a welding of the nanomanipulator 825 to the Fin 810a.

Figure 9C:
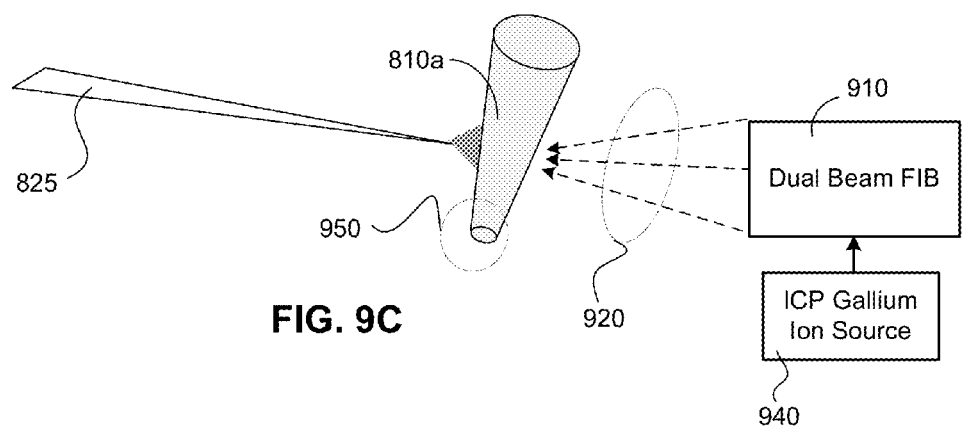

At 710, the tip 950 (FIG. 9C) of the defective Fin 810a (FIG. 9C) that is welded 915 (FIG. 9C) to the nanomanipulator 825 (FIG. 9C) is sharpened using the focused Gallium (Ga) ion beam 920 (FIG. 9C). More particularly, as a result of this Gallium based FIB milling, the defective Fin 810a (FIG. 9C) or sample may be shaped in the form of a cone, whereby the sharpened tip 950 (FIG. 9C) may have a diameter in the range of about 20-100 nm. The diameter of the sharpened tip 950 (FIG. 9C) may, generally, be formed to any value which facilitates successfully accomplishing an APT-based ablation process on the tip 950 (FIG. 9C).

At 712, an APT process is carried out on the prepared Fin 810a (FIG. 9C) sample in order to determine a 3D image of the material constituting the Fin 810a (FIG. 9C), Using APT, for example, Boron distribution and concentration within the Fin 810a (FIG. 9C) may be determined for evaluating the threshold voltage of the device. It may be appreciated that although the exemplary embodiment refers to preparing one or more Fin samples that have been determined to be defective based on a C-V measurement, non-defective samples may also be prepared in the same or similar manner for APT measurements and subsequent characteristic evaluation.

Figure 10:
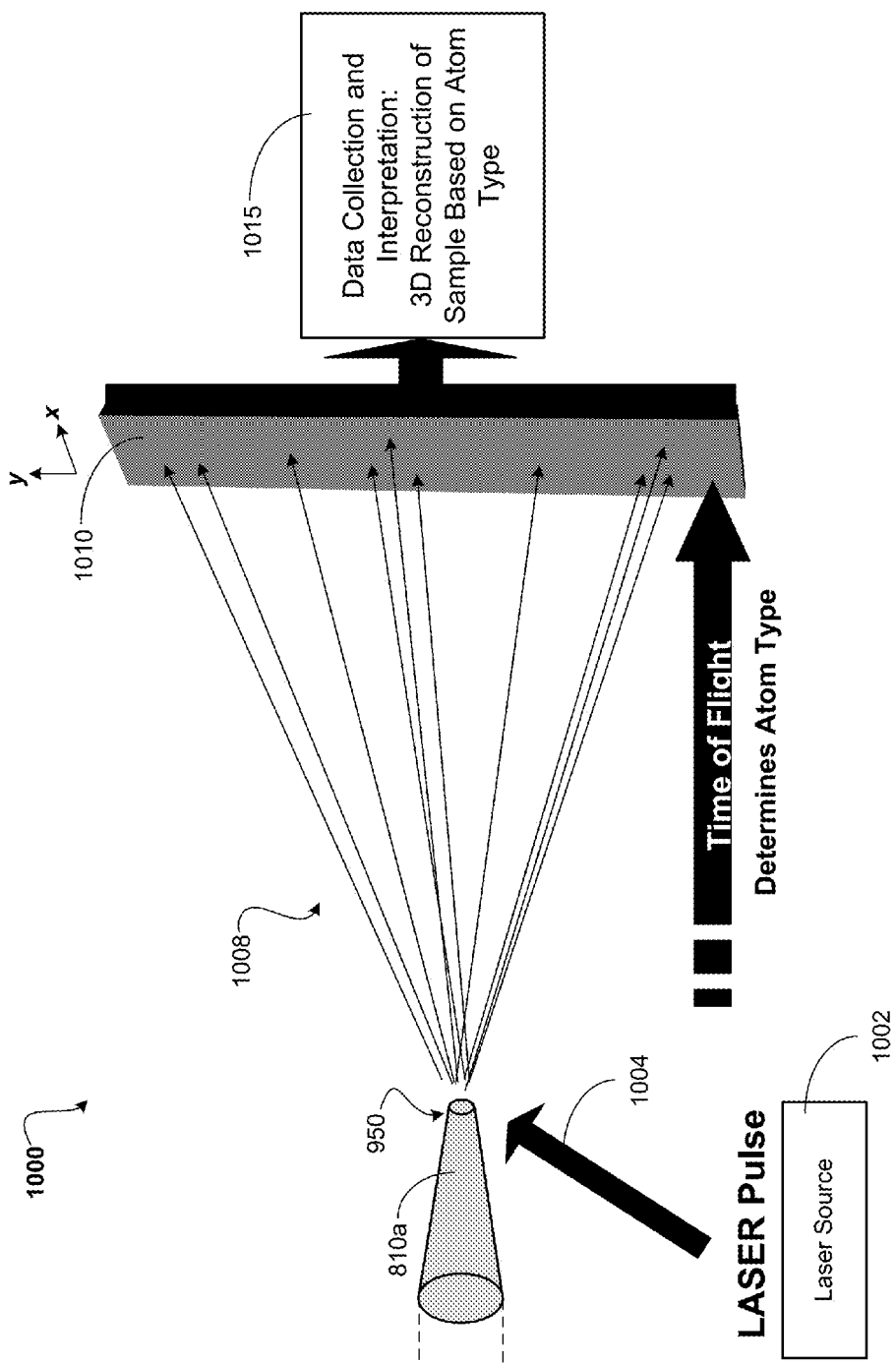
FIG. 10 illustrates an APT process for determining a 3D image of the prepared Fin of FIGS. 9A-9C according to an exemplary embodiment.

Referring to FIG. 10, an APT measurement process for determining a 3D image of the prepared sample Fin 810a is depicted. As conventionally known, the APT process may provide 3D imaging and chemical composition measurements at the atomic scale. As shown, the tip 950 of the prepared sample 810a is irradiated by a laser pulse 1004 generated by a laser source 1002 of an APT apparatus 1000. Since the hardmask materials 810a, 810b (FIG. 8A) of the prepared sample 810a are removed using the low voltage (<300 eV) collimated ion beam process associated with the apparatus 100 of FIG. 1, self destruction of the prepared sample 810a during the laser pulsing of the APT process may be mitigated. Moreover, the sharpening of the Fin sample 810a (FIG. 9C) tip 905 (FIG. 9C) is carried out by the low voltage (<1000 eV) dual beam Gallium FIB 910 (FIG. 9C), which may further avoid amorphization damage and/or gallium contamination. As the prepared sample 810a is irradiated by the laser pulse 1004, atoms 1008 from the tip 950 of the prepared sample 810a are removed layer by layer (i.e., ablation). The removed atoms are projected onto a position sensitive detector (PSD) 1010, based on a generated electrostatic field between the position sensitive detector 1010 and the tip 950 of the prepared sample 810a. The time-of-flight of the atoms (i.e., ions) from the instant the laser 1002 is pulsed to the time they arrive at the position sensitive detector 1010 may be used to determine the mass over charge ratio (i.e., m/q). Also, the x, y coordinates of the detected atoms on the position sensitive detector 1010 may be utilized to reconstruct (3D) the original position of the atoms corresponding to the tip 950 of the prepared Fin sample 810a. As depicted, a processing unit 1015 may, therefore, collect the positional data from the position sensitive detector 1010 and reconstruct a 3D image of the tip 950 of the prepared Fin sample 810a by atom type.

Further, as described above, the micromanipulator may be used to both remove a sample (e.g., Fin 810a) from a 3D semiconductor structure (e.g., FinFet 800) and to retain connectivity with the sample via the low energy (<1000 eV) Gallium focused ion beam. The micromanipulator may further hold the sample during subsequent tip sharpening of the sample prior to the APT process.

The one or more exemplary embodiments described above may provide, among other things, an apparatus and method of generating C-V characteristic measurements for discrete devices, such as, FinFet device (3D structures), MOSFET devices, and embedded DRAM devices, etc. The measurements may therefore, for example, facilitate detecting charge extraction of trapped charge in gate dielectric films and high-K gate films, enabling threshold $V_t$ measurements of FinFET and planar MOSFET devices, detecting AC defects that are undetectable by conventional DC measurements, measuring eDRAM deep trench capacitor measurements, enabling contact level capacitance measurements of devices, as well measuring and evaluating dopant concentration and distribution issues associated with 3D discrete structures such as FinFETs. Moreover, the one or more exemplary embodiments described above may provide, among other things, enhanced sample preparation for APT processes.

The descriptions of the various embodiments of the present invention have been presented for purposes of illustration, but are not intended to be exhaustive or limited to the embodiments disclosed. Many modifications and variations will be apparent to those of ordinary skill in the art without departing from the scope and spirit of the described embodiments. The terminology used herein was chosen to best explain the principles of the one or more embodiment, the practical application or technical improvement over technologies found in the marketplace, or to enable others of ordinary skill in the art to understand the embodiments disclosed herein.

What is claimed is:

1. A method for atom probe tomography (APT) sample preparation from a three-dimensional (3D) field effect transistor device formed within a semiconductor structure, the method comprising:
   measuring a capacitance-voltage (C-V) characteristic for the 3D field effect transistor device;
   identifying, based on the measured capacitance-voltage (C-V) characteristic, a Fin structure corresponding to the 3D field effect transistor device;
   detaching the identified Fin structure from the 3D field effect transistor device using a nanomanipulator probe tip;
   welding the detached Fin to the nanomanipulator probe tip using an incident focused ion beam having a voltage of less than about 1000 eV; and
   applying the incident focused ion beam having a voltage of less than about 1000 eV to a tip of the Fin that is welded to the nanomanipulator probe tip, wherein the tip of the Fin is sharpened by the focused ion beam.

2. The method of claim 1, further comprising:
   applying an atomic probe tomography measurement on the Fin that is sharpened by the focused ion beam.

3. The method of claim 1, wherein the tip of the Fin is sharpened to a diameter in the range of about 20 nm-100 nm.

4. The method of claim 1, wherein the measuring of the capacitance-voltage (C-V) characteristic for the 3D field effect transistor device comprises:
   exposing first and second contact regions associated with the 3D field effect transistor device;
   coupling a high-frequency impedance probe having a frequency range of about 5 Mhz to about 110 Mhz to an impedance analyzer;
   coupling the high-frequency impedance probe to a first and a second atomic force probe tip;
   coupling, using an atomic force microscope, the first atomic force probe tip to the exposed first contact region;
   coupling, using the atomic force microscope, the second atomic force probe tip to the exposed second contact region; and
   measuring the C-V characteristic for the 3D field effect transistor device on the impedance analyzer, the impedance analyzer applying an operating frequency corresponding to the frequency range of about 5 Mhz to about 110 Mhz to the first and second contact regions of the 3D field effect transistor device using the high-frequency impedance probe.

5. The method of claim 4, further comprising:
   an XYZ manipulation stage that holds the high-frequency impedance probe, the XYZ manipulation stage manipulating the XYZ position of the high-frequency impedance probe for optimizing the measured C-V characteristic for the 3D field effect transistor device by controlling both a first physical tension associated with a first electrical conductor coupled to a ground connection of the high-frequency impedance, and a second physical tension associated with a second electrical conductor coupled to a signal conductor of the high-frequency impedance probe.

6. The method of claim 4, wherein the exposing of the first and second contact regions comprises:
   applying a voltage in the range of about 50 eV to less than 300 eV to an inductively coupled Argon ion source operating at a radio frequency;
   generating, from the Argon ion source, a collimated ion beam incident on a surface corresponding to the first and second contact regions for planar removal of layers of the surface; and
   exposing the first and second contact regions underlying the surface using an end-point detector based on the planar removal of the layers.

7. The method of claim 6, wherein the generated collimated ion beam is incident on the surface of the semiconductor structure at an angle of about 3-12 degrees.

8. The method of claim 6, wherein the radio frequency (RF) comprises a 1.4 MHz signal.

9. The method of claim 6, wherein the end-point detector comprises a secondary ion mass spectroscopy (SIMS) detector.

10. The method of claim 6, wherein the planar removal of layers comprises removing layers of silicon nitride using etch selective hexafluoroethane ($C_2F_6$) gas.

11. The method of claim 6, wherein the planar removal of layers comprises removing layers of silicon oxide using etch selective tetrafluoromethane ($CF_4$) gas.

12. The method of claim 6, wherein the planar removal of layers comprises removing layers of copper metallization.

13. The method of claim 6, wherein the exposed first and second contact regions comprises tungsten studs coupled to the 3D field effect transistor device.

14. The method of claim 1, wherein the C-V measurement is utilized to determine doping concentration in the Fin structure.

15. The method of claim 4, wherein the high-frequency impedance probe is coupled to a first and a second electrical conductor, the first electrical conductor coupled to the ground connection of the high-frequency impedance probe and the second electrical conductor coupled to the signal conductor of the high-frequency impedance probe.

16. The method of claim 15, wherein the first electrical conductor is coupled to the first atomic force probe tip and the second electrical conductor is coupled to the second atomic force probe tip.

17. A method for atom probe tomography (APT) sample preparation from a three-dimensional (3D) field effect transistor device formed within a semiconductor structure, the method comprising:
   applying a voltage in the range of about 50 eV to less than 300 eV to an inductively coupled Argon ion source operating at a radio frequency;
   generating, from the Argon ion source, a collimated ion beam incident on a crystalline surface of the semiconductor structure for planar removal of layers of the crystalline surface, wherein the collimated ion beam minimizes surface amorphization of the crystalline surface of the semiconductor structure;
   exposing first and second contact regions underlying the crystalline surface associated with the 3D field effect transistor device using an end-point detector based on the planar removal of the layers;
   coupling a high-frequency impedance probe having a frequency range of about 5 Mhz to about 110 Mhz to an impedance analyzer;
   coupling the high-frequency impedance probe to a first and a second atomic force probe tip;
   coupling, using an atomic force microscope, the first atomic force probe tip to the exposed first contact region;
   coupling, using the atomic force microscope, the second atomic force probe tip to the exposed second contact region;
   measuring the C-V characteristic for the 3D field effect transistor device on the impedance analyzer, the impedance analyzer applying an operating frequency corresponding to the frequency range of about 5 Mhz to about 110 Mhz to the first and second contact regions associated with the 3D field effect transistor device using the high-frequency impedance probe; and
   detaching, based on the measured C-V characteristic, a Fin structure from the 3D field effect transistor device using a nanomanipulator probe tip, the detached Fin being both welded to the nanomanipulator probe tip and shaped using an incident focused ion beam having a voltage of less than about 1000 eV.

18. The method of claim 17, wherein the incident focused ion beam is generated by an inductively coupled Gallium ion source having a voltage in the range of about 500 eV-1000 eV.

19. A method for atom probe tomography (APT) sample preparation from a three-dimensional (3D) field effect transistor device formed within a semiconductor structure, the method comprising:
   identifying, based on a capacitance-voltage (C-V) characteristic measurement, a Fin structure corresponding to the 3D field effect transistor device;
   removing a hardmask layer from a top surface of the Fin structure using a collimated ion beam generated by applying a voltage in the range of about 50 eV to less than 300 eV to an inductively coupled Argon ion source operating at a radio frequency;
   applying a metallic coating to the Fin structure;
   detaching the coated Fin structure from the 3D field effect transistor device using a nanomanipulator probe tip;
   welding the detached coated Fin to the nanomanipulator probe tip using an incident focused ion beam having a voltage of less than about 1000 eV; and
   applying the incident focused ion beam having a voltage of less than about 1000 eV to a tip of the Fin that is welded to nanomanipulator probe tip, wherein the tip of the Fin is sharpened by the incident focused ion beam.

20. The method of claim 19, wherein the metallic coating comprises nickel, cobalt, and ruthenium, the metallic coating having a thickness of about 10 nm-30 nm.

* * * * *